(12) United States Patent
Dekel et al.

(10) Patent No.: US 10,898,272 B2
(45) Date of Patent: Jan. 26, 2021

(54) VISUALIZING NAVIGATION OF A MEDICAL DEVICE IN A PATIENT ORGAN USING A DUMMY DEVICE AND A PHYSICAL 3D MODEL

(71) Applicant: Biosense Webster (Israel) Ltd., Yokneam (IL)

(72) Inventors: Zvi Dekel, Zichron Yaakov (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 757 days.

(21) Appl. No.: 15/671,979

(22) Filed: Aug. 8, 2017

(65) Prior Publication Data

US 2019/0046271 A1 Feb. 14, 2019

(51) Int. Cl.
| | |
|---|---|
| *A61B 34/20* | (2016.01) |
| *G09B 23/30* | (2006.01) |
| *A61B 1/267* | (2006.01) |
| *G16H 50/00* | (2018.01) |
| *A61B 90/00* | (2016.01) |
| *A61B 17/24* | (2006.01) |
| *A61B 17/00* | (2006.01) |

(52) U.S. Cl.
CPC .............. *A61B 34/20* (2016.02); *A61B 1/267* (2013.01); *A61B 17/24* (2013.01); *A61B 90/37* (2016.02); *G09B 23/30* (2013.01); *G16H 50/00* (2018.01); *A61B 2017/00716* (2013.01); *A61B 2034/2051* (2016.02); *A61B 2034/2065* (2016.02); *A61B 2090/367* (2016.02); *A61B 2090/368* (2016.02); *A61B 2090/374* (2016.02); *A61B 2090/3762* (2016.02)

(58) Field of Classification Search
CPC ......... A61B 34/20; A61B 1/267; A61B 17/24; A61B 90/37; A61B 2017/00716; A61B 2090/3762; A61B 2090/374; A61B 2090/368; A61B 2090/367; A61B 2034/2065; A61B 2034/2051; G16H 50/00; G09B 23/30; G06T 19/003
See application file for complete search history.

(56) References Cited

U.S. PATENT DOCUMENTS

| | | | |
|---|---|---|---|
| 5,391,199 | A | 2/1995 | Ben-Haim |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 2002/0065455 | A1 | 5/2002 | Ben-Haim et al. |

(Continued)

FOREIGN PATENT DOCUMENTS

WO WO 1996/005768 2/1996

OTHER PUBLICATIONS

European Search Report and Written Opinion dated Jan. 7, 2019 for Application No. 18187662.4, 5 pages.

*Primary Examiner* — Peter Luong
(74) *Attorney, Agent, or Firm* — Frost Brown Todd LLC

(57) ABSTRACT

A method includes, receiving a first sequence of first positions of a medical device that moves in a body of a patient. The first positions of the medical device are visualized to a user, by automatically moving a dummy device, external to the body, in a second sequence of second positions that mimics the first sequence.

20 Claims, 2 Drawing Sheets

(56) References Cited

U.S. PATENT DOCUMENTS

| | | |
|---|---|---|
| 2003/0120150 A1 | 6/2003 | Govari |
| 2004/0068178 A1 | 4/2004 | Govari |
| 2010/0268068 A1 | 10/2010 | Vass et al. |
| 2011/0301760 A1* | 12/2011 | Shuster ................. G06T 19/003 700/264 |
| 2012/0280988 A1 | 11/2012 | Lampotang et al. |
| 2013/0108999 A1 | 5/2013 | Gillies et al. |
| 2013/0172906 A1* | 7/2013 | Olson .................... A61B 34/74 606/130 |
| 2015/0093734 A1* | 4/2015 | Kaouk ................... A61B 34/10 434/267 |
| 2015/0325151 A1 | 11/2015 | Tuchschmid et al. |
| 2016/0008083 A1 | 1/2016 | Kesten et al. |

* cited by examiner

VISUALIZING NAVIGATION OF A MEDICAL DEVICE IN A PATIENT ORGAN USING A DUMMY DEVICE AND A PHYSICAL 3D MODEL

FIELD OF THE INVENTION

The present invention relates generally to tracking a medical device in a patient organ, and particularly to methods and systems for assisting navigation of the medical device using a dummy device and a three-dimensional (3D) physical model.

BACKGROUND OF THE INVENTION

In various medical procedures, a visual 3D model is displayed for assisting a physician in navigating a medical tool in an organ of a patient.

For example, U.S. Patent Application Publication 2010/0268068, issued as U.S. Pat. No. 7,996,063 on Aug. 9, 2011, describes a system and method for a medical intervention procedure within a cardiac chamber having an imaging system to obtain image data of the cardiac chamber and to create a 3D model from that image data. The patent application further describes an interventional system to register the 3D model with a real-time image of the cardiac chamber and to display the 3D model, and an interventional tool positioned in the cardiac chamber to be displayed upon the interventional system and to be navigated in real-time over the registered 3D model.

U.S. Patent Application Publication 2012/0280988, issued as U.S. Pat. No. 9,251,721 on Feb. 2, 2016, describes an interactive mixed reality simulator that includes a virtual 3D model of internal or hidden features of an object, a physical model or object being interacted with, and a tracked instrument used to interact with the physical object.

SUMMARY OF THE INVENTION

An embodiment of the present invention that is described herein provides a method including receiving a first sequence of first positions of a medical device that moves in a body of a patient. The first positions of the medical device are visualized to a user, by automatically moving a dummy device, external to the body, in a second sequence of second positions that mimics the first sequence.

In some embodiments, receiving the first sequence includes receiving first orientations of the medical device at the respective first positions, and moving the dummy device further includes orienting the dummy device in second orientations at the respective second positions, so as to mimic the first orientations. In other embodiments, the medical device includes an ear-nose-throat (ENT) tool or a guidewire. In yet other embodiments, automatically moving the dummy device includes moving the dummy device in a physical three-dimensional (3D) model that models at least part of the body of the patient, the physical 3D model is external to the body.

In an embodiment, the method includes producing the physical 3D model by receiving one or more anatomical images of the at least part of the body, and deriving, based on the one or more anatomical images, instructions for producing the physical 3D model. In another embodiment, producing the physical 3D model includes printing the physical 3D model, based on the instructions, using a 3D printer. In yet another embodiment, automatically moving the dummy device includes controlling a robot, coupled to the dummy device, to move the dummy device to the second positions.

In some embodiments, automatically moving the dummy device includes controlling a projector that projects a marker at the second positions. In other embodiments, the first positions are provided in a first coordinate system, and the second positions are provided in a second coordinate system, and the method includes registering between the first coordinate system and the second coordinate system.

In an embodiment, automatically moving the dummy device includes moving the dummy device in a three-dimensional (3D) scene, external to the body, which models at least part of the body of the patient. In another embodiment, the method includes constructing the 3D scene by receiving one or more anatomical images of the at least part of the organ, and deriving, based on the one or more anatomical images, instructions for constructing the 3D scene.

There is additionally provided, in accordance with an embodiment of the present invention, an apparatus that includes an interface and a processor. The interface is configured to receive a first sequence of first positions of a medical device that moves in a body of a patient. The processor is configured to visualize the first positions of the medical device to a user, by automatically moving a dummy device, external to the body, in a second sequence of second positions that mimics the first sequence.

The present invention will be more fully understood from the following detailed description of the embodiments thereof, taken together with the drawings in which:

DETAILED DESCRIPTION OF EMBODIMENTS

Overview

Figure 1:
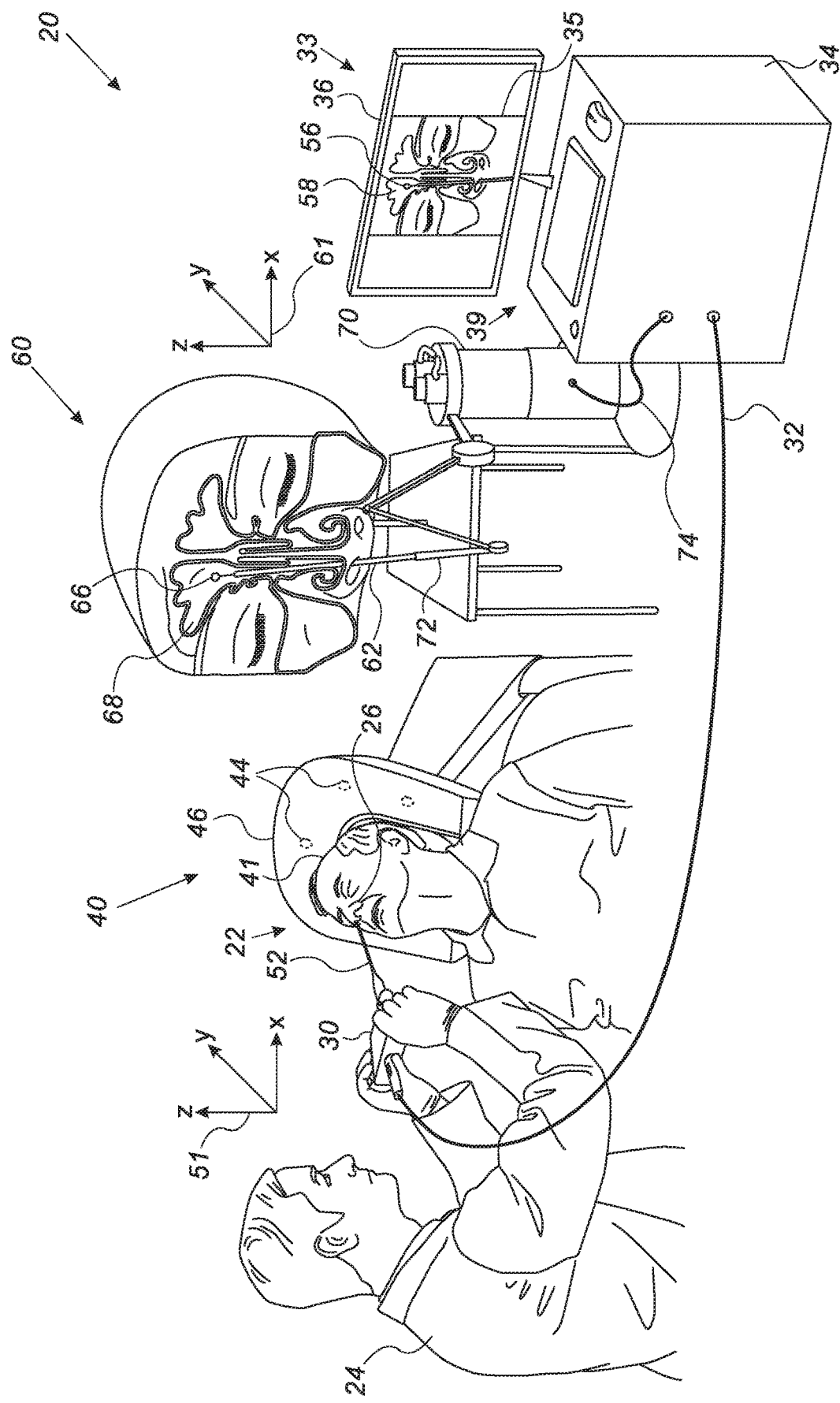
FIG. 1 is a schematic, pictorial illustration of a sinuplasty surgical system, in accordance with an embodiment of the present invention.

Some medical procedures, such as sinuplasty, require visualization of a medical device relative to an organ of a patient into which the medical device is inserted.

Embodiments of the present invention that are described hereinbelow provide improved techniques for visualizing a medical device relative to a patient organ, e.g., an ear-nose-throat (ENT) tool relative to a sinus of a patient head in a sinuplasty procedure. The disclosed techniques apply a dummy device that mimics the movement of the ENT tool but has no medical functionality. In the context of the present disclosure and in the claims, the terms "tool" and "device" are used interchangeably and refer to any suitable medical and/or dummy devices.

In some embodiments, in a preparation procedure that is typically applied prior to the sinuplasty procedure, a processor of a sinuplasty system receives multiple two-dimensional (2D) computerized tomography (CT) images depicting respective slices of the patient head. The processor is configured to derive, based on the CT images, a virtual three-dimensional (3D) model of ENT organs of the patient, e.g., the patient sinus. The processor is further configured to generate instructions for producing a physical 3D model of at least part of the patient head that comprises the sinus. A 3D printer produces the physical 3D model based on the printing instructions, such that every volume pixel (voxel) of the physical 3D model is registered with a corresponding voxel of the virtual 3D model of the CT image.

In the present context, the term "virtual 3D model" refers to a computerized representation of the organ, typically stored in a suitable memory accessible to the processor. The term "physical 3D model" refers to a tangible, material reproduction of the organ.

In some embodiments, first and second position sensors of a position tracking system are coupled to respective distal tips of the ENT tool and of the dummy tool. In an embodiment, the processor is configured to register between the coordinate systems used by the CT system and by the position tracking system. In this embodiment, the positions of the ENT tool and of the dummy tool are both measured in the coordinate system of the position tracking system, and displayed on a display of the sinuplasty system and on the physical 3D model.

In applying the medical procedure, a physician inserts the ENT tool into the patient nose. The ENT tool can be regarded as moving in a first sequence of first positions and orientations in the patient body. In some embodiments, a robot, which is coupled to the dummy tool, inserts the dummy tool into the physical 3D model. The robot moves the dummy tool in the physical 3D model, in a second sequence of second positions and orientations that mimic the respective first positions and orientations of the medical device. In this manner, the positions and orientations of the medical tool, which is hidden from view, are automatically and continuously visualized to the physician by the movement of the dummy tool within the physical 3D model.

The disclosed techniques are particularly important in medical procedures, such as sinuplasty, carried out in highly branched organs. In such procedures, the disclosed techniques enable accurate navigation to a target location, and help in reducing navigation errors, thereby reducing the overall cycle time of the procedure.

Furthermore, the disclosed techniques obviate the need to irradiate the patient with hazardous X-ray radiation during the procedure, so as to verify the position and orientation of the medical tool relative to the organ in question.

System Description

FIG. 1 is a schematic, pictorial illustration of a sinuplasty surgical system 10, in accordance with an embodiment of the present invention. In an embodiment, system 20 comprises a console 33, which comprises a processor 34, input devices 39 and a user display 36.

In an embodiment, in a preparation procedure, processor 34 is configured to receive one or more computerized tomography (CT) images depicting respective segmented two-dimensional (2D) slices of a head 41 of a patient 22, obtained using an external CT system (not shown). The term "segmented" refers to displaying various types of tissues identified in each slice by measuring respective attenuation of the tissues in the CT system.

In some embodiments, processor 34 is configured to construct, based on the CT images, a virtual three-dimensional (3D) model of head 41. In other embodiments, a processor of the CT system may construct the virtual 3D model. In some embodiments, processor 34 is configured to display from among the CT images, one or more selected slices, such as an image 35, on display 36. In the example of FIG. 1, image 35 is a sectional view of frontal and maxillary sinuses, such as a sinus 58, and a nasal passage in turbinate tissue of head 41.

In an embodiment, processor 34 is further configured to derive, based on the CT images, instructions for producing a physical three-dimensional (3D) model 60 of at least part of head 41. The physical 3D model may be produced using a 3D printer or any other suitable producing technique. Note that every volume pixel (voxel) of physical 3D model 60 is registered with a corresponding voxel of the virtual 3D model since both models are based on the CT images of head 41.

In some embodiments, model 60 may comprise a physical model of a stack of multiple adjacent slices of head 41 comprising the sectional view displayed in image 35, such that a sinus 68 of physical 3D model 60 models physically the sectional view of sinus 58. In other embodiments, physical 3D model 60 comprises only a region of interest (ROI) of the patient ENT system, such as sinus 58, and optionally tissue located several millimeters or centimeters in the periphery of the ROI.

In some embodiments, system 20 comprises a medical device, such as a guidewire or a surgical ear-nose-throat (ENT) tool 52, which is controlled by a handle 30, and is configured to perform a sinuplasty procedure, e.g., in sinus 58 of head 41.

Visualization of Medical Device Navigation Using Dummy Device in Physical 3D Model During the sinuplasty procedure, a physician 24 may insert ENT tool 52 through nose 26, so as to navigate the distal tip of ENT tool 52 into sinus 58. In an embodiment, physician 24 may navigate tool 52 into sinus 58, using a position tracking system that uses a coordinate system 51. In this embodiment, processor 34 is configured to register between coordinate system 51 and a coordinate system 61 of the CT system. In this embodiment, the position of ENT tool may be displayed on display 36, e.g., as a marker overlaid on image 35.

Note that image 35 depicts only a 2D slice of the ROI (e.g., a sectional view of sinus 58) and may therefore contain less information than required for carrying out the sinuplasty procedure at a precise desired location within sinus 58. In some embodiments, system 20 comprises a dummy tool 62, such as a physical device having a size and shape that resembles ENT tool 52 (as shown in FIG. 1) or any other suitable size and shape, or a marker projected on physical 3D model 60, or any other suitable type of a dummy tool.

In some embodiments, dummy tool 62 is coupled to an arm 72 of a robot 70, which is configured to move arm 72 so as to navigate the distal tip of dummy tool 62, into a target location in sinus 68 of physical 3D model 60.

In some embodiments, system 20 comprises a magnetic position tracking system, which is configured to track the position and orientation of one or more position sensors, such as position sensors 56 and 66. In the example of FIG. 1, position sensor 56 is coupled to ENT tool 52 and position sensor 66 is coupled to dummy tool 62.

In some embodiments, the magnetic position tracking system comprises magnetic field-generators 44 and position sensors 56 and 66. Sensors 56 and 66 are configured to generate position signals in response to sensed external magnetic fields from field generators 44. In an embodiment, processor 34 is configured to map the position of sensors 56 and 66, in coordinate system 51 of the magnetic position system.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1, issued as U.S. Pat. No. 7,729,742 on Jun. 1, 2010; and 2004/0068178 A1, now abandoned, whose disclosures are all incorporated herein by reference.

In some embodiments, position sensor 56, which is coupled to the distal tip of ENT tool 52, is tracked in head 41 of patient 22, such that the coordinates of sensor 56 are reported in coordinate system 51 of the position tracking system. In some embodiments, sensor 66, which is coupled to the distal tip of dummy tool 62, is reported with reference to coordinate system 51, and tracked in physical 3D model 60, which is registered with coordinate system 61 of the CT system. In some embodiments, processor 34 is configured to register between coordinate systems 51 and 61 so as to enable moving dummy tool 62 within physical 3D model 60, to a position and orientation that mimics a respective position and orientation of tool 52 in head 41.

In the present example, system 20 comprises a location pad 40, which comprises multiple field-generators 44 fixed on a frame 46. In the exemplary configuration shown in FIG. 1, pad 40 comprises five field-generators 44, but any other suitable number of field-generators 44 can be used.

In some embodiments, pad 40 is placed under head 41 of patient 22, such that field-generators 44 are located at fixed, known positions external to the patient. In an embodiment, console 33 further comprises a driver circuit (not shown) configured to drive field-generators 44 with suitable signals so as to generate magnetic fields in a predefined working volume around head 41.

In an embodiment, processor 34 is typically a general-purpose computer comprising suitable front end and interface circuits for receiving data from external sources, such as the CT imaging system. Processor 34 is further configured to receive position signals from sensors 56 and 66, via respective cables 32 and 74 connected to handle 30 and robot 70, respectively, and for controlling other components of system 20.

In some embodiments, processor 34 is configured to receive from sensor 56 a first sequence of positions and orientations of the distal tip of tool 52 that moves in head 41. Based on the first sequence, processor 34 is configured to set robot 70 to automatically move dummy tool in a second sequence of positions and orientations within physical 3D model 60, such that each position and orientation of dummy tool 62 mimics a respective position and orientation of ENT tool 52.

In some embodiments, processor 34 is configured to register between dummy tool 62 and ENT tool 52, e.g., in coordinate system 51. In these embodiments, position sensor 66 may be omitted from the configuration of system 20, or alternatively used as control means for verifying the location of dummy tool 62.

In some embodiments, processor 34 is configured to display respective positions of sensors 56 and 66 in image 35 and in physical 3D model 60, simultaneously. In an embodiment, processor 34 is further configured to display data, such as virtual markers and various measurements, overlaid on image 35 and/or elsewhere on display 36. In this embodiment, physician 24 can use physical 3D model 60 for navigating tool 52, and the data displayed on display 36, to carry out the sinuplasty procedure.

In alternative embodiments, instead of receiving the one or more CT images, processor 34 is configured to receive one or more images acquired using another suitable anatomical imaging technique, such as magnetic resonance imaging (MRI) having a respective coordinate system, and to register between the coordinate systems of the MRI system and the position tracking system, as described above.

In alternative embodiments, physical 3D model 60 may comprise any suitable type of 3D model, instead of the printed 3D physical model. For example, in an embodiment, processor 34 is configured to construct a 3D scene, such as a hologram constructed based on the CT images, and to display the hologram on a suitable holographic display. In these embodiments, processor 34 is further configured to mimic the position of the ENT tool 52 by projecting a marker on the 3D scene, such that the marker is indicative of the distal tip or any other suitable part of the dummy tool. Alternatively, a physical dummy tool, such as dummy tool 62, may be used for mimicking the position and orientation of ENT tool 52 in the scene.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Figure 2:
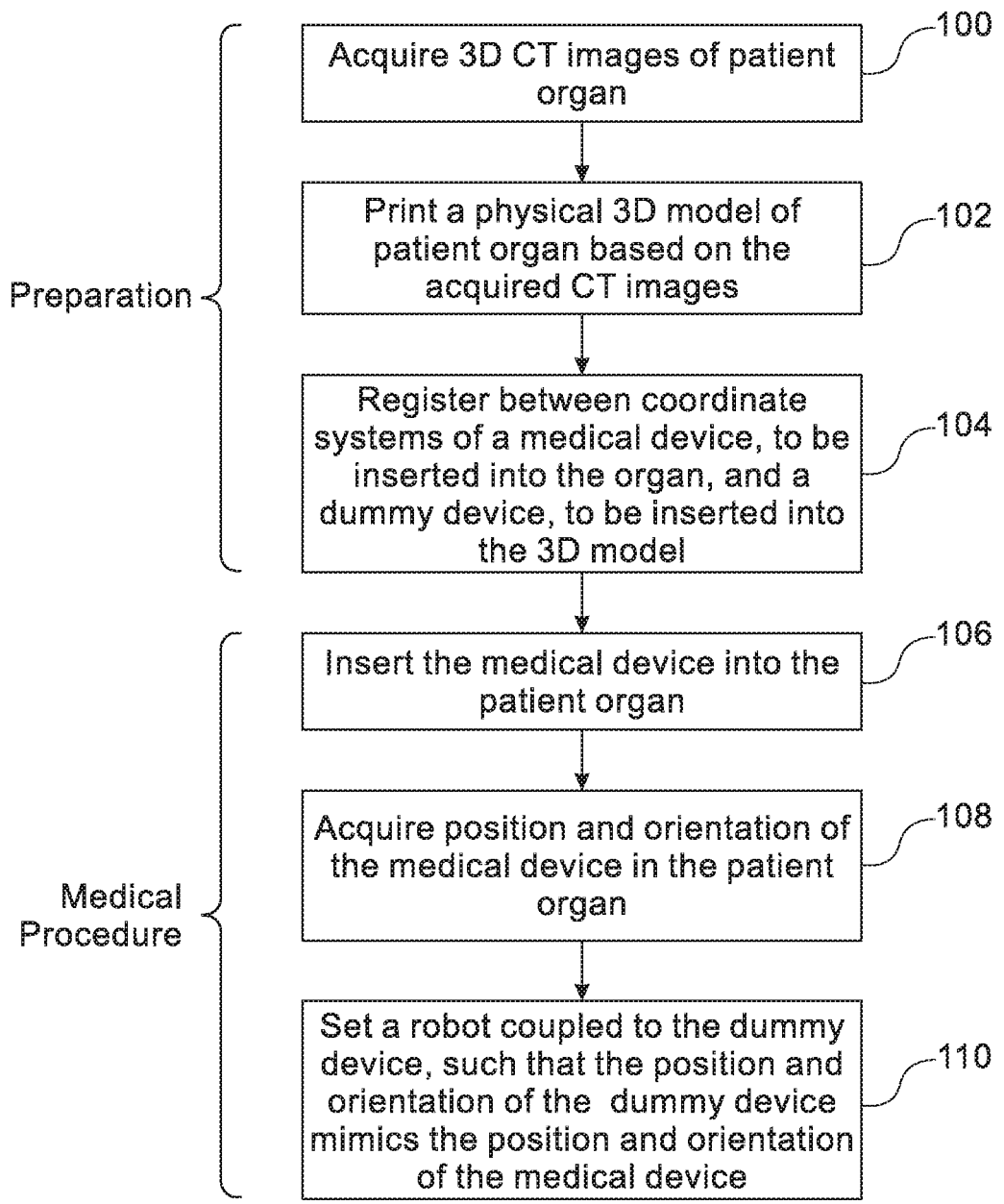
FIG. 2 is a flow chart that schematically illustrates a method for visualizing the position and orientation of a medical device in an organ, in accordance with an embodiment of the present invention.

FIG. 2 is a flow chart that schematically illustrates a method for visualizing the position and orientation of ENT tool 52 in head 41, in accordance with an embodiment of the present invention. In some embodiments, the method comprises a preparation procedure carried out before the medical procedure, and operations carried out during the medical procedure.

The preparation procedure begins with processor 34 receiving one or more anatomical images of head 41, at an image acquisition step 100. In some embodiments, an anatomical imaging system, such as a CT system, acquires multiple 2D slices of sectional view images of head 41. In some embodiments, the 2D slices are segmented so as to identify various types of tissues in each slice.

In some embodiments, processor 34 is configured to construct, based on the 2D slices, a virtual 3D model of head 41, or to receive the virtual 3D model of head 41 from the CT system.

At a physical 3D model formation step 102, processor 34 derives, based on the received CT images, instructions for producing physical 3D model 60 of at least part of head 41, which is produced using a 3D printer or any other suitable producing technique. Note that every voxel of physical 3D model 60 is registered with a corresponding voxel of the virtual 3D model described in image acquisition step 100, since both models are derived from the same CT images of head 41. Therefore, physical 3D model 60 is registered with coordinate system 61 of the CT system.

In some embodiments, physical 3D model 60 comprises a physical model of the sectional view displayed in image 35, such that sinus 68 of model 60 is a physical 3D model of the sectional view of sinus 58.

At a registration step 104, which concludes the preparation procedure, processor 34 registers between coordinate system 51 of the position tracking system and coordinate system 61 of the CT system. This registration scheme supports tracking the position and orientation of dummy tool 62 (which is reported in coordinate system 51) in physical 3D model 60 (which is registered with coordinate system 61.) This registration scheme further supports reporting the position and orientation of ENT tool 52 and of dummy tool 62, using position signals received from sensors 56 and 66, respectively and typically simultaneously.

At an ENT tool insertion step 106, which is the first step of the medical procedure in the method of FIG. 2, physician 24 inserts ENT tool 52, having position sensor 56 coupled to its distal tip, into head 41 of patient 22.

At a sequence acquisition step 108, processor 34 receives from sensor 56, via handle 30 and cable 32, a first sequence of position signals, indicative of the positions and orientations of the distal tip of ENT tool 52 in head 41. At a 3D visualization step 110, which concludes the method, processor 34 sets robot 70 to visualize the positions and orientations of ENT tool 52 to physician 24, by automatically moving dummy tool 62 within 3D model 60, in a second sequence of positions and orientations that mimics the first sequence of the positions and orientations of ENT tool 52.

In other embodiments, dummy tool 62 may comprise a projector (not shown) that replaces robot 70, arm 72, physical dummy tool 62 and sensor 66 shown in FIG. 1 above. The projector, which is controlled by processor 34, is configured to receive positions and instructions from processor 34, and to visualize the positions of ENT tool 52 by automatically moving a marker, projected on 3D model 60, in a third sequence of positions that mimics the first sequence of the positions of ENT tool 52.

In yet other embodiments, system 20 comprises a holographic display (not shown) configured to display 3D scenes, such as holograms. The holographic display may replace the physical 3D model, such as printed physical 3D model 60. In these embodiments, processor 34 displays a 3D scene on the holographic display, such that the 3D scene comprises at least the ROI (e.g., sinus 58), constructed based on the CT images.

In an embodiment, processor 34 (e.g., using a projector) projects dummy tool 62 is projected on the 3D scene (e.g., using a different color of light) as a holographic object or as a marker. In another embodiment, processor 34 moves a physical dummy tool, such as dummy tool 62, within the hologram using the configuration depicted in FIG. 1 above.

In alternative embodiments, at least one of position sensors 56 and 66 may be couple to respective tools 52 and 62 at any suitable location different than the distal tip. For example, ENT tool 52 may comprise a hollow tube configured to draw material from sinus 58. In this configuration, sensor 56 may be mounted on the distal end of tool 52, at a predefined offset from the distal tip, such that the offset is held in processor 34 for the operations described above. In these embodiments, processor 34 is configured to register between tools 52 and 62 using this offset, and possibly, an additional offset for the position of sensor 66 relative to the distal tip of tool 62.

In the embodiments described herein, the dummy device (e.g., dummy tool 62) mimics both the positions and the orientations of the medical device (e.g., ENT tool 52.) In alternative embodiments, the dummy device may mimic only the positions (and not the orientations) of the medical device. This implementation has reduced functionality, but may simplify the system (e.g., the robot) considerably.

Although the embodiments described herein mainly address sinuplasty procedures, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   (a) receiving a first sequence of first positions of a medical device in response to the medical device moving in a body of a patient during a medical operation on the patient; and
   (b) after receiving the first sequence, visualizing the first positions of the medical device to a user, by automatically moving a dummy device, external to the body, in a second sequence of second positions that mimics the first sequence during the medical operation on the patient.

2. The method according to claim 1, wherein receiving the first sequence comprises receiving first orientations of the medical device at the respective first positions, and wherein moving the dummy device further comprises orienting the dummy device in second orientations at the respective second positions, so as to mimic the first orientations.

3. The method according to claim 1, wherein the medical device comprises an ear-nose-throat (ENT) tool or a guidewire.

4. The method according to claim 1, wherein automatically moving the dummy device comprises moving the dummy device in a physical three-dimensional (3D) model that models at least part of the body of the patient, wherein the physical 3D model is external to the body.

5. The method according to claim 4, further comprising producing the physical 3D model by receiving one or more anatomical images of the at least part of the body, and deriving, based on the one or more anatomical images, instructions for producing the physical 3D model.

6. The method according to claim 5, wherein producing the physical 3D model comprises printing the physical 3D model, based on the instructions, using a 3D printer.

7. The method according to claim 1, wherein automatically moving the dummy device comprises controlling a robot, coupled to the dummy device, to move the dummy device to the second positions.

8. The method according to claim 1, wherein automatically moving the dummy device comprises controlling a projector that projects a marker at the second positions.

9. The method according to claim 1, wherein the first positions are provided in a first coordinate system, and the second positions are provided in a second coordinate system, the method further comprising registering between the first coordinate system and the second coordinate system.

10. The method according to claim 1, wherein automatically moving the dummy device comprises moving the dummy device in a three-dimensional (3D) scene, external to the body, which models at least part of the body of the patient.

11. The method according to claim 10, further comprising constructing the 3D scene by receiving one or more anatomical images of the at least part of the organ, and deriving, based on the one or more anatomical images, instructions for constructing the 3D scene.

12. An apparatus, comprising:
    (a) a medical device positioned within a surgical environment and configured to move in a body of a patient during a medical operation on the patient;
    (b) a dummy device positioned within the surgical environment and configured to move external to the body of the patient during the medical operation on the patient;
    (c) an interface, which is configured to receive a first sequence of first positions of the medical device in response to the medical device moving in the body of the patient during the medical operation on the patient; and
    (d) a processor, which is configured to visualize the first positions of the medical device to a user, by automatically moving the dummy device, external to the body, in a second sequence of second positions that mimics the first sequence after the interface receives the first sequence during the medical operation on the patient.

13. The apparatus according to claim 12, further comprising a position tracking system including a position sensor, wherein the interface is configured to receive from the position sensor of the position tracking system, first orientations of the medical device at the respective first positions, and wherein the processor is further configured to orient the dummy device in second orientations at the respective second positions, so as to mimic the first orientations.

14. The apparatus according to claim 12, wherein the medical device comprises an ear-nose-throat (ENT) tool or a guidewire.

15. The apparatus according to claim 12, further comprising a physical three-dimensional (3D) model that models at least part of the body of the patient, wherein the physical 3D model is external to the body of the patient, wherein the processor is configured to move the dummy device in the physical three-dimensional (3D) model.

16. The apparatus according to claim 12, further comprising a robot coupled to the dummy device and configured to move the dummy device to the second positions, wherein the processor is configured to control the robot.

17. The apparatus according to claim 12, further comprising a projector configured to project a marker at the second positions, wherein the processor is configured to control the projector.

18. The apparatus according to claim 12, wherein the first positions are provided in a first coordinate system, and the second positions are provided in a second coordinate system, and wherein the processor is configured to register between the first coordinate system and the second coordinate system.

19. The apparatus according to claim 12, further comprising a three-dimensional (3D) scene that models at least part of the body of the patient, wherein the 3D scene is external to the body, wherein the processor is configured to automatically move the dummy device in the three-dimensional (3D) scene.

20. A method, comprising:
    (a) moving a medical device in a body of a patient;
    (b) in response to moving the medical device in the body of the patient, receiving a first sequence of first positions of the medical device; and
    (c) in response to receiving the first sequence, automatically moving a dummy device within at least one of a physical three-dimensional (3D) model or a three-dimensional (3D) scene, wherein the at least one of a physical 3D model or a 3D scene models at least part of the body of the patient and is positioned external to the body of the patient, wherein automatically moving the dummy device includes moving the dummy device in a second sequence of second positions that mimics the first sequence;
    (d) observing the dummy device moving in the second sequence within the at least one of a physical 3D model or a 3D scene; and
    (e) moving the medical device in the body of the patient based on observing the dummy device moving in the second sequence within the at least one of a physical 3D model or a 3D scene.

* * * * *